US010306925B2

(12) United States Patent
Borkovec et al.

(10) Patent No.: US 10,306,925 B2
(45) Date of Patent: Jun. 4, 2019

(54) AEROSOL GENERATING COMPONENT FOR AN ELECTRONIC SMOKING DEVICE AND ELECTRONIC SMOKING DEVICE

(71) Applicant: FONTEM HOLDINGS 1 B.V., Amsterdam (NL)

(72) Inventors: Vaclav Borkovec, Hamburg (DE); Stefan Biel, Hamburg (DE); Diego Gonzalez, Amsterdam (NL)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 365 days.

(21) Appl. No.: 15/066,595

(22) Filed: Mar. 10, 2016

(65) Prior Publication Data

US 2016/0262456 A1 Sep. 15, 2016

(30) Foreign Application Priority Data

Mar. 13, 2015 (EP) .................................... 15158976

(51) Int. Cl.
*A61M 15/06* (2006.01)
*H05B 1/02* (2006.01)
*A24F 47/00* (2006.01)

(52) U.S. Cl.
CPC ......... *A24F 47/008* (2013.01); *H05B 1/0202* (2013.01); *H05B 1/0244* (2013.01)

(58) Field of Classification Search
None
See application file for complete search history.

(56) References Cited

U.S. PATENT DOCUMENTS 5,743,251 A * 4/1998 Howell ................ A61M 11/041 128/200.14
6,234,167 B1 * 5/2001 Cox .................. A61M 15/0003 128/200.14
6,491,233 B2 * 12/2002 Nichols ................ A61M 11/041 239/128
6,715,487 B2 * 4/2004 Nichols ................. A61M 15/00 128/200.14
6,886,557 B2 * 5/2005 Childers ........... A61M 15/0065 128/200.14
6,923,179 B2 * 8/2005 Gupta .................. A61M 11/041 128/200.14

(Continued)

FOREIGN PATENT DOCUMENTS

CN 202664231 U 1/2013
CN 202738816 U 2/2013

(Continued)

OTHER PUBLICATIONS

European Patent Office, Combined European Search and Examination Report issued in EP Patent Application No. 15158976.9.

(Continued)

*Primary Examiner* — Thor S Campbell
(74) *Attorney, Agent, or Firm* — Perkins Coie LLP; Kenneth H. Ohriner

(57) ABSTRACT

An aerosol generating component (2) for an electronic smoking device and an electronic smoking device with an aerosol generating component (2) are provided. In order to improve smoking experience, the aerosol generating component (2) is adapted to generate two aerosols with different particle sizes.

14 Claims, 3 Drawing Sheets

(56) References Cited

U.S. PATENT DOCUMENTS

| | | | | |
|---|---|---|---|---|
| 7,367,334 | B2 * | 5/2008 | Faison, Jr. | A61M 11/041 128/203.12 |
| 7,500,479 | B2 * | 3/2009 | Nichols | A61M 15/00 128/200.21 |
| 9,271,528 | B2 * | 3/2016 | Liu | A24F 47/008 |
| 2007/0068523 | A1 * | 3/2007 | Fishman | A61M 16/0051 128/203.12 |
| 2012/0048266 | A1 | 3/2012 | Alelov | |
| 2013/0340775 | A1 | 12/2013 | Juster | |
| 2014/0000638 | A1 * | 1/2014 | Sebastian | A24F 47/008 131/328 |
| 2014/0060556 | A1 | 3/2014 | Liu | |
| 2014/0190503 | A1 * | 7/2014 | Li | A61M 15/06 131/329 |
| 2014/0209105 | A1 * | 7/2014 | Sears | F22B 1/28 131/328 |
| 2014/0261488 | A1 | 9/2014 | Tucker | |
| 2014/0366898 | A1 * | 12/2014 | Monsees | A24F 47/008 131/329 |
| 2016/0371590 | A1 * | 12/2016 | Blackley | G06N 5/04 |
| 2017/0251727 | A1 * | 9/2017 | Nielsen | A24F 47/008 |

FOREIGN PATENT DOCUMENTS

| | | | |
|---|---|---|---|
| CN | 203633508 | U | 6/2014 |
| CN | 203884699 | U | 10/2014 |
| EP | 2754361 | A1 | 7/2014 |
| WO | 2005107837 | A1 | 11/2005 |
| WO | 2010107613 | A1 | 9/2010 |

OTHER PUBLICATIONS

United Kingdom Intellectual Property Office, Combined Search and Examination Report under Sections 17 and 18(3) issued in GB Patent Application No. GB1507668.0 (dated Jun. 30, 2015).

* cited by examiner

AEROSOL GENERATING COMPONENT FOR AN ELECTRONIC SMOKING DEVICE AND ELECTRONIC SMOKING DEVICE

PRIORITY CLAIM

This application claims priority to EP Patent Application No. 15158976.9 filed Mar. 13, 2015, and now pending.

FIELD OF THE INVENTION

The field of the invention is aerosol generating components for electronic smoking devices and electronic smoking devices with aerosol generating components.

Electronic smoking devices, such as electronic cigarettes, have become well-known products. Generally, an electronic smoking device has an aerosol generating component that is adapted to form an aerosol from a material to be inhaled by a user of the smoking device. The aerosol generating component may be supplied with operating power by an electric power source, such as a rechargeable battery, which may be part of the smoking device. When a sensor of the smoking device detects a user inhaling on a mouth piece of the smoking device, the aerosol generating component may automatically be supplied with operating power in order to generate the aerosol. Alternatively, a manual actuator may be used to manually initiate that the aerosol generating component is supplied with operating power in order to generate the aerosol. The manual actuator is for example a button or a switch.

Flavor products preferably comprise flavored materials added to a liquid. Flavored materials are for example esters, such as isoamyl acetate, linalyl acetate, isoamyl propionate, linalyl butyrate and the like or natural essential oils as plant essential oils, such as spearmint, peppermint, cassia, jasmine and the like or animal essential oils, such as musk, amber, civet, castor and the like or simple flavoring materials, such as anethole, limonene, linalool, eugenol and the like or hydrophilic flavour components such as a leaf tobacco extract or natural plant flavoring materials such as licorice, St. John's wort, a plum extract, a peach extract and the like or acids such as a malic acid, tartaric acid, citric acid and the like or sugars such as glucose, fructose, isomerized sugar and the like or polyhydric alcohols such as propylene glycol, glycerol, sorbitol and the like. It is also possible to combine different flavored materials as mentioned above into new flavored materials. Moreover, it is possible to adsorb any flavor onto a solid material and to use this material as flavored material within an electronic smoking device according to the present invention.

SUMMARY OF THE INVENTION

It is desirable to provide two different materials that can be inhaled at the same time, the materials for example being a flavour product and a nicotine product.

In one aspect of the present invention, an aerosol generating component for an electronic smoking device is provided, wherein the aerosol generating component is adapted to generate two aerosols, a particle size of a first of the aerosols differing from a particle size of a second of the aerosols, and wherein the aerosol generating component comprises a first atomizer that is adapted to generate the first aerosol, and a second atomizer that is adapted to generate the second aerosol. In another aspect of the present invention, an aerosol generating component of an electronic smoking device is an aerosol generating component according to the invention.

An advantage of the aerosol generating component according to the present invention is that the particle size can be preselected for chosen materials to be inhaled, such that the materials can be transported to desired locations within the respiratory system of the user of the smoking device. For example, in case a first of the materials to be inhaled is a flavour product, the particle size of the flavour product in the aerosol can be chosen to be large, e.g. larger than 5 μm, such that the first material is more likely to be deposited higher in the respiratory track (such as in the buccal and nasal cavity where the taste and smell receptors are located) and can improve the user's taste experience more efficiently. The second material to be inhaled may be a nicotine product, for example a product that contains a certain amount of nicotine, wherein the size of the particles of the second product in the aerosols may be smaller than the particle size of the first product and for example between 1 and 3 μm, such that the nicotine containing particles are more likely to be deposited in the lower respiratory tract where the transfer to the bloodstream is most efficient. Hence, less nicotine needs to be inhaled by the user in order to achieve a desired effect, compared to a traditional electronic cigarette where the particle size is not optimised for nicotine transfer to the blood.

The particle size preferably is a typical particle size of the material to be inhaled in the aerosol. For example, the particle size may be the mean particle size of the particles of one of the products to be inhaled. Alternatively, the particle size distribution may have its maximum value at the typical particle size of the particles of one of the products to be inhaled. The particle sizes may be specified as mass median aerodynamic diameter.

The characteristics, features and advantages of this invention and the manner in which they are obtained as described above, will become more apparent and be more clearly understood in connection with the following description of exemplary embodiments, which are explained with reference to the accompanied drawings.

BRIEF DESCRIPTION OF THE DRAWINGS

In the drawings, same element numbers indicate same elements in each of the views.

DETAILED DESCRIPTION OF THE DRAWINGS

Figure 1:
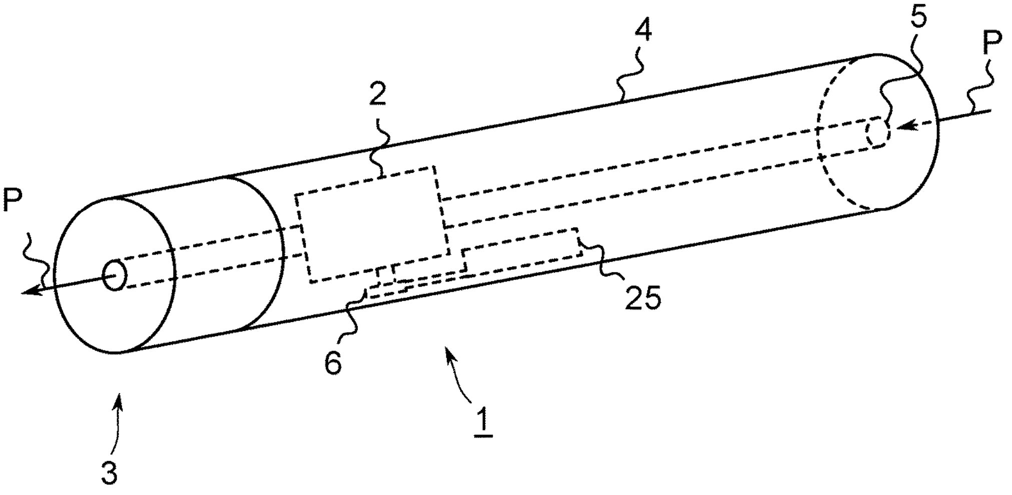
FIG. 1 is a schematic view of an electronic smoking device according to an embodiment of the present invention with the aerosol generating component.

FIG. 1 shows a schematic cross-sectional view of an electronic smoking device 1 with an aerosol generating component 2 according to the present invention. The electronic smoking device 1 comprises a mouth piece 3 for providing materials to be inhaled to a user of the electronic smoking device 1.

The aerosol generating component 2 is preferably arranged in a housing 4 of the electronic smoking device 1, the housing 4 allowing gas to flow along a flow path P, e.g. from an intake 5 to the aerosol generating component 2, through the aerosol generating component 2 and from the aerosol generating component 2 to the mouth piece 3. The electronic smoking device 1 may comprise a puff sensor 6, which is triggered in case the user takes a puff. The puff sensor 6 may be connected to the aerosol generating component 2, which can begin to generate aerosol as soon as the puff is detected by the puff sensor 6. Further, the puff sensor 6 may be connected to an electric power source 7, e.g. a battery that can supply operation power to the aerosol generating component 2. As an alternative to the puff sensor 6, a button or switch may be provided in order to manually trigger the aerosol generating component 2.

Figure 2:
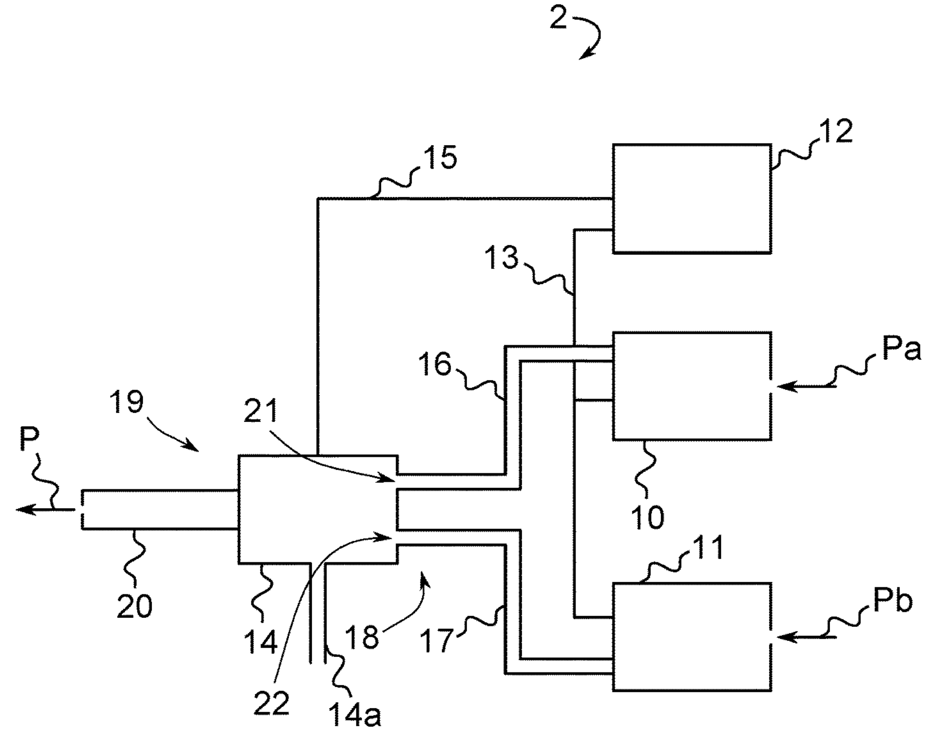
FIG. 2 is a schematic view of an aerosol generating component according to an embodiment of the invention.

FIG. 2 shows a schematic view of the aerosol generating component 2 according to the present invention. The aerosol generating component 2 is adapted to generate two aerosols, a particle size of a first of the aerosols differing from a particle size from a second of the aerosols. The particle sizes can be easily measured, for example by generating the two aerosols and by measuring the particle sizes of these two aerosols. For example, the same materials may be used to generate the two aerosols for controlling that the aerosol generating component 2 is adapted to generate two aerosols with different particle sizes. Furthermore, in case different materials are to be atomized or vaporized in order to generate the two aerosols for inhalation with the electronic smoking device 1, the particle sizes of these aerosols can, again, easily be determined, for example by known particle size measurement methods.

The aerosol generating component 2 according to the invention comprises a first atomizer 10 that is adapted to generate the first aerosol, and a second atomizer 11, that is adapted to generate the second aerosol. For example, the first atomizer 10 and the second atomizer 11 may have different predetermined operational states, which result in the different particle sizes of the aerosols. By providing two atomizers 10, 11, each of the atomizers 10, 11 can easily be adapted to generate the respective aerosol from the material or the materials to be inhaled. The initial flow path P may partly be led into the first atomizer 10 as a first partial flow path Pa, and into the second atomizer 11 as a second partial flow path Pb.

The aerosol generating component 2 may comprise a control unit 12 for controlling process properties of at least one or even both of the first and the second atomizers 10, 11. In order to be able to control process properties of the first and/or the second atomizer 10, 11, the control unit 12 may be connected to at least one or to both of the atomizers 10, 11, e.g. in a signal transmitting manner, for example by at least one signal conductor 13.

Furthermore, the aerosol generating component 2 may comprise a blending apparatus 14 for blending the first with the second aerosol, the blending apparatus 14 being adapted such that the quantity of at least one of the first and the second aerosols to be blended with another one of the first and the second aerosols is changeable. Optionally, the blending apparatus 14 may additionally blend the two aerosols with gas, e.g. ambient air. In case the blending apparatus 14 is adapted to blend the two aerosols with ambient air, the aerosol generating component 2 may comprise an ambient air pipe 14*a* that opens to the environment of the aerosol generating component 2 and in particular of the electronic smoking device 1, and that is connected to the blending apparatus 14 in a gas conducting manner.

Along the partial flow paths Pa, Pb, ambient air mixed with the materials to be inhaled in order to form the two aerosols can be led to the blending apparatus 14, in which the two aerosols are blended, i.e. mixed, with each other or with each other and with ambient air.

Again, the mixing ratio of the gas and the aerosols may be changeable by the blending apparatus 14. Hence, the blending apparatus 14 may be adjustable, such that the quantity of at least one of the aerosols can be changed. For example, the blending apparatus 14 may be adapted such that a user of the electronic smoking device can select mixing ratios at the blending apparatus 14. Alternatively, at least one predefined mixing ratio may be provided, e.g. by the smoking device or by a container comprising the material to be inhaled. The blending apparatus 14 may be adapted to adjust mixing ratios of the two aerosols, such that one of the aerosols is not at all mixed with the other one and only the other one is led towards the mouth piece 3. Alternatively or additionally, mixing ratios of 25/75, 50/50, 75/25 and/or 100/0 or ratios therebetween can be accomplished by the blending apparatus 14. Furthermore, mixing ratios of the blended aerosols with gas may be selectable to mixing ratios of 25/75, 50/50, 75/25 and/or 100/0 or ratios therebetween by the blending apparatus 14. In order to be able to change the mixing ratio, the control unit 12 may be connected to the blending apparatus 14, preferably in a control signal transmitting manner, for example by another signal conductor 15.

The blending apparatus 14 may be connected to each of the atomizers 10, 11 in an aerosol conducting manner, for example by aerosol conductors 16, 17, which may be provided as pipes or tubes. Between the atomizers 10, 11 and the blending apparatus 14, the partial flow paths Pa, Pb may each extend through one of the aerosol conductors 16, 17. In particular, the atomizers 10, 11 may be connected to an input side 18 of the blending apparatus 14. An output side 19 of the blending apparatus 14 can be connected to the mouth piece 3 of the electronic smoking device 1, if the aerosol generating component 2 is part of the electronic smoking device 3. To be able to connect the aerosol generating component 2 with the mouth piece 3, the aerosol generating component 2 may comprise an adapter or fitting 20, which may be connected to the output side 19 of the blending apparatus 14 in an aerosol conductive manner. At least in or behind the adapter or fitting 20, the partial flow paths Pa, Pb may be rejoined to the flow path P. Alternatively, the adapter 11 may comprise an inner tube connected directly to aerosol conductor 7, and a concentric outer tube connected directly to aerosol conductor 8, with no blending apparatus used. In this case, concentric flows of first and second aerosols may be provided, with the outer flow surrounding the inner flow, thereby reducing deposition of the fluid particles of the inner flow in the mouth and the back of the throat. This design may allow better deep lung delivery of the inner aerosol flow. It may also be used to shield the tongue from an off-tasting inner aerosol.

The aerosol generating component 2 may comprise at least one orifice 21, 22, through which the aerosol of one of the atomizers 10, 11 may stream along one of the partial flow paths Pa, Pb and through one of the aerosol conductors 16, 17. The at least one orifice 21, 22 is preferably arranged at the input side 18 of the blending apparatus 14. In order to be able to adapt the mixing ratios, the inner diameter of the at least one orifice may be changeable.

Figure 3:
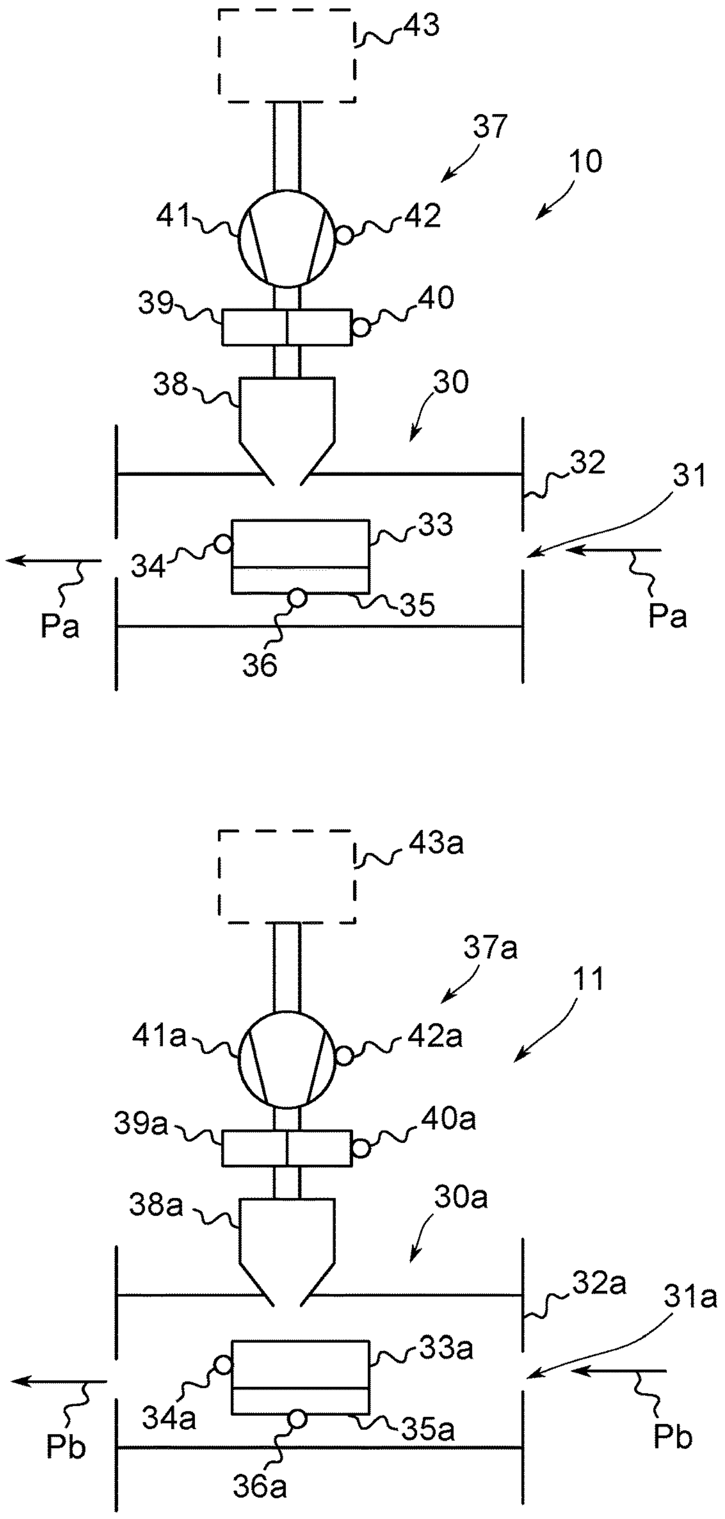
FIG. 3 is a schematic view of two atomizers of the aerosol generating component according to another possible embodiment of the invention.

FIG. 3 shows a schematic cross-sectional view of the two atomizers 10, 11 of the aerosol generating component 2 according to the invention. The second atomizer 11 may have the same basic structure as the first atomizer 10, but may differ from the first atomizer 10 in that it is adapted to generate an aerosol with a different particle size than the first atomizer 10.

The atomizers 10, 11 may each comprise a mixing chamber 30, 30*a* for mixing atomized material with gas, the gas preferably being ambient air and led into the respective mixing chamber 30, 30*a* via one of the partial flow paths Pa, Pb. Hence, each of the atomizers 10, 11 may comprise a mixing chamber 30, 30*a* that is separate from the other mixing chamber 30*a*, 30, such that the atomized materials can independently of each other be mixed with gas in the respective mixing chamber 30, thereby generating aerosols with different particle sizes.

The first atomizer 10 and the second atomizer 11 may each comprise an inlet opening 31, 31*a* for supplying gas into the respective mixing chamber 30, 30*a*. Each of the partial flow paths Pa, Pb may lead through the respective inlet opening 31, 31*a* into the respective mixing chamber 30, 30*a*. The partial flow paths Pa, Pb are preferably fed by the flow path P. The mixing chambers 30, 30*a* are preferably provided with outlet openings, via which the atomized particles mixed with the gas, thereby forming the aerosol, can leave the mixing chamber 30 along the respective partial flow path Pa, Pb, for example towards the mouth piece 3.

The inlet opening 31 of the first atomizer 10 may be formed or dimensioned to allow for generation of the first aerosol, and the inlet opening 31*a* of the second atomizer 11 may be formed or dimensioned to allow for generation of the second aerosol. Preferably, the two inlet openings 31, 31*a* are differently dimensioned, such that different gas streams, e.g. with different forms, directions and/or flow rates, can flow into the mixing chambers 30, 30*a*. For example, the directions may be the directions of the partial flow paths Pa, Pb at the respective inlet opening 31, 31*a* and inside of the mixing chambers 30, 30*a*. Due to the flow characteristics of the gas, e.g. represented by the Reynolds number, which may be mainly determined by the form and/or the dimension of the inlet openings 31, 31*a*, an effective influence of the particle sizes is achieved. The gas, namely, influences the particle size, as e.g. a higher flow may result in a turbulent gas stream, which may cause a higher interaction between particles, again resulting in larger particles. Cooling the atomized material, for example by mixing the atomized material with gas, i.e. gaseous dilution, influences the condensation of atomized material into liquid droplets, i.e. the particles, which influences the particle size, too. Hence, the particle sizes of the aerosols can be preselected in hardware by the forms or dimensions of the inlet openings 31, 31*a*. High airflow results in high dilution, which reduces the interaction between particles and stops them growing in size. Low airflow results in low dilution, which increases the probability of the particles growing.

According to an embodiment, the predefined size of the particles in the aerosol generated with the first or the second atomizer 10, 11 is changeable. Hence, in order to be able to change the size of the particles, the inlet opening 31, 31*a* of at least one of the first atomizer 10 and the second atomizer 11 may be changeable.

The size of the respective inlet opening 31, 31*a* may be selectable by the user and may be changeable manually. Alternatively or additionally, the size of the inlet opening 31, 31*a* may be predetermined, for example by the smoking device 1. In particular, an inner diameter of the inlet opening 31, 31*a* may be changeable, such that different amounts of gas can be led into the mixing chamber 30.

At least one of the inlet openings 31, 31*a* may be formed by an iris diaphragm with a variable inner diameter. Alternatively or additionally, at least one of the first atomizer 10 and the second atomizer 11 may comprise a gas inlet element 32, 32*a* which comprises the inlet opening 31, 31*a*. The gas inlet element 32, 32*a* may be changeable against another gas inlet element 32, 32*a*, which may have another inlet opening 31, 31*a* that is differently dimensioned.

Alternatively or additionally, the gas inlet element 32, 32*a* may be provided with at least two inlet openings 31, 31*a*, that may be brought in communication, hence in a gas conductive contact, with an inner volume of the mixing chamber 30, 30*a* as desired, i.e. one or the other or even both of the inlet openings 31, 31*a*, for example at choice of the user or according to a predetermined information provided by the smoking device. In case two inlet openings 31, 31*a* are gas conductively connected to the inner volume of the mixing chamber 30, 30*a*, the combined surface of the inlet openings 31, 31*a* defines a surface through which gas can be led into the mixing chamber 30, 30*a*. Hence, even if the gas inlet element 32, 32*a* comprises at least two inlet openings 31, 31*a* with identical dimensions, the gas stream into the mixing chamber 30, 30*a* can be easily changed.

The gas inlet element 32, 32*a* may be formed as a plate that is moveable with respect to the mixing chamber 30, 30*a* or even exchangeable. Alternatively, the inlet openings 31, 31*a* may be formed by gas ducts of the gas inlet element 32, 32*a*, the gas inlet element 32, 32*a* preferably being moveable with respect to the mixing chamber 30, 30*a* or even exchangeable.

The inlet openings 31, 31*a* may separately from each other be connected with the environment of the aerosol generating component 2 or even of the electronic smoking device 1, in order to decouple gas or air streams led through the inlet openings 31, 31*a*. Alternatively, the inlet openings 31, 31*a* of both of the atomizers 10, 11 may be connected to a common external inlet opening of the aerosol generating component 2 or the electronic smoking device 1 in order to reduce complexity of design. For example, the inlet openings 31, 31*a* are both connected or connectable to the intake 5.

In order to better influence the particle size independent of the dimension of the inlet opening 31, 31*a* or in addition to the dimensioning of the inlet opening 31, 31*a*, the first atomizer 10 and the second atomizer 11 may each comprise an atomizing element 33, 33*a* for atomizing material for one of the aerosols. The atomizing element 33 of the first atomizer 10 is preferably adapted to allow for generation of the first aerosol, and the atomizing element 33*a* of the second atomizer 11 is preferably adapted to allow for generation of the second aerosol.

Each of the atomizing elements 33, 33*a* may be provided with a control contact 34, 34*a*, such that the respective atomizing element 33, 33*a* can be connected to the control unit 12, preferably in a control signal transmitting manner.

The atomizing elements 33, 33*a* may be formed as ultrasonic atomizers which may be differently dimensioned or operated. For example, the ultrasonic atomizers may be operated at different frequencies and/or amplitudes in order to generate the different particle sizes.

Alternatively, at least one or even both of the atomizing elements 33, 33*a* may be a heating element for atomizing material for the aerosols by evaporation, the heating elements being adapted to allow for generation of the aerosols with the different particle sizes. For example, the heating element of the first atomizer 10 may have a first predetermined operation temperature, and the heating element of the second atomizer 11 may have a second predetermined operation temperature different from the first predetermined operation temperature. Possible predefined operating temperatures of the heating elements are between 130° C. and 300° C., for example around 220° C.

Different temperatures influence the particle size. For example, warmer atomized materials tend to have larger particle sizes than colder atomized materials, as an increase of the temperature results in an increased particle interaction and agglomeration of the particles, resulting in larger particles.

For example, the heating elements may be heating coils. The heating elements may comprise a wick, which prevents liquid materials to be atomized from forming drops which drop off of the respective heating element. Alternatively the heating element may not comprise a wick and can, instead, have a geometry which acts like a wick material to keep the liquid in contact with the wire through cohesive properties of the liquid.

Furthermore, the atomizing elements 33, 33*a* of the atomizers 10, 11 may have different forms or comprise different surfaces in order to allow for the generation of the aerosols with different particle sizes. In particular, the forms and/or the surfaces of the atomizing elements 33, 33*a* may be adapted to most effectively vaporise the respective material to be atomized, for example liquids. Optionally or additionally, the sizes of the atomizing elements 33, 33*a* of the first and the second atomizers 10, 11 may differ from each other, for example in order to adapt the heating efficiency of the respective material to be atomized, thereby influencing the particle sizes of the atomized materials in the aerosols. Higher power delivery results in a higher temperature, which increases the rate of vaporization, such that larger particles are created. Lower power delivery results in a lower temperature, which results in smaller particles. The temperature achieved in the material to be atomized and in particular to be vaporized can also be controlled by mass of the material that impinges the atomizing elements.

The size, shape and/or operation properties of at least one of the atomizing elements 33, 33*a* may be changeable in order to be able to adjust the particle size of one of the aerosols. The operation properties may be electrical power or frequency of an operation power fed to the atomizing elements 33, 33*a*.

At least one of the atomizers 10, 11 may comprise a temperature sensor 35, 35*a* for sensing the temperature of the heating element, the temperature sensor 35, 35*a* being connected to the control unit 12, for example in a sensor signal transmitting manner. A temperature sensor converts a temperature into a signal that is representative for the temperature. Exemplary temperature sensors are negative or positive temperature coefficient resistors. The temperature of the heating elements can be controlled by the control unit 12, such that the temperature of the heating elements is within ±10° C. or even within ±1° C. of the respective predetermined operation temperature. In order to be connectable to the control unit 12, the temperature sensor 35, 35*a* preferably comprises a signal contact 36, 36*a*.

Due to the temperature sensor 35, 35*a*, the temperature of the respective atomizing element 33, 33*a* can be controlled and even influenced by the control unit 12, such that the respective atomizing element 33, 33*a* is operated at the predetermined operation temperature, which may be pre-set in the control unit 12. The predetermined operation state of the respective atomizing element 33, 33*a*, in particular the predetermined operation temperature, may be controlled during atomizing the material to be atomized, such that for example the temperature of the respective atomizing element 33, 33*a* decreases less due to the atomizing.

The quantity of the material to be atomized influences the temperature of the atomized materials due to the different thermal mass to which the respective atomizing element 33, 33*a* is exposed. Thus, due to the temperature sensor 35, 35*a*, the temperature of the respective heating element can be influenced and for example be maintained within a pre-set temperature range during evaporation.

Hence, the predetermined operation temperatures may be stored or storable or may be represented by data or rules stored in the control unit 12. In case different materials shall be atomized at the user's selection, the predetermined operation temperatures can depend on the material to be atomized and may be selected by the user, provided by the smoking device 1 or by information provided with the materials to be inhaled.

In order to provide the material to be atomized, the first atomizer 10 and the second atomizer 11 may each comprise a supply apparatus 37, 37*a* for supplying the material to be atomized to the respective atomizing element 33, 33*a*. The supply apparatus 37 of the first atomizer 10 may be adapted to allow for generation of the first aerosol and the supply apparatus 37*a* of the second atomizer 11 may be adapted to allow for generation of the second aerosol.

In particular, the supply apparatus 37 of the first atomizer 10 may be adapted to supply a first quantity of the material to be inhaled in one puff, and the supply apparatus 37*a* of the second atomizer 11 may be adapted to supply a second quantity of the material to be inhaled in one puff, the second quantity differing from the first quantity. For example, at least one of the supply apparatuses 37,37*a* is adapted to supply quantities between 0.05 μl to 5 μl, for example between 0.1 μl and 2 μl, in particular of 1 μl. The other one of the supply apparatuses 37,37*a* may be adapted to supply a different quantity than the one of the supply apparatuses 37,37*a*, the quantities being between 0.05 μl to 5 μl, for example between 0.1 μl and 2 μl, in particular of 1 μl The control unit 12 may be connected to at least one and in particular to both of the supply apparatuses 37, 37*a*, for example in a control signal transmitting manner. The control unit 12 may be adapted to control the quantity of the material to be atomized and subsequently inhaled, that is supplied to the atomizing element 33, 33*a*.

Alternatively or additionally, the control unit 12 can be adapted to activate at least one of the supply apparatuses 37, 37*a* after at least one of the atomizing elements 33, 33*a* has reached a predetermined operation state. For example, the control unit 12 may activate one or both of the supply apparatuses 37, 37*a* after one or both of the heating elements have reached the predetermined operation temperature.

The supply apparatuses 37, 37*a* may each comprise a nozzle 38, 38*a* that is directed towards the respective atomizing element 33, 33*a*. For example, the nozzle 38, 38*a* may be arranged above the respective atomizing element 33, 33*a* in a direction of gravity, if the electronic smoking device 1 is held in a predefined smoking position. The nozzle 38, 38*a* may be a small orifice, which is dimensioned to dispense and e.g. spray liquid materials to be atomized onto the respective atomizing element 33, 33*a*. Via the nozzle 38,38*a*, material to be atomized, in particular liquids, can be dispensed onto the respective atomizing element 33, 33*a* in an extensive manner such that the respective atomizing element 33, 33*a* is uniformly coverable with the material to be atomized. In many applications, gravity forces are negligible relative to fluid forces, so that the arrangement of the nozzle relative to gravity is not relevant.

Preferably, the nozzles 38, 38*a* of the first and the second atomizers 10, 11 are different nozzles 38, 38*a*, which may be differently dimensioned. Alternatively or additionally, the distance between the nozzle 38 and the atomizing element 33 of the first atomizer 10 may be different to the distance between the nozzle 38*a* and the atomizing element 33*a* of the second atomizer 11 in order to achieve that aerosols with different particle sizes are generated.

The quantity of the dispensed material to be atomized by the respective atomizing element 33, 33*a* can be adapted to the atomizing properties of the respective atomizing element 33, 33*a*, such that the material to be atomized is atomized with the desired particle size, even after mixing the atomized material with gas, e.g. ambient air.

A valve 39, 39*a* may be arranged upstream of the nozzle 38, 38*a*, the valve 39, 39*a* adjusting the flow of material to be atomized to the nozzle 38, 38*a*. The valve 39, 39*a* may be provided with a control contact 40, 40*a* that may be connectable or connected to the control unit 12, such that supply of the material to be atomized to the nozzle 38, 38*a* can be controlled by the control unit 12.

The valve 39, 39*a* may be arranged between the respective nozzle 38, 38*a* and a pump 41, 41*a* for transporting the material to be atomized via the optional valve 39, 39*a* towards the nozzle 38, 38*a*. The pump 41, 41*a* may be manually actuatable by the user, e.g. when the user presses the manual actuator. Alternatively, the pump 41, 41*a* may be electrically driven. In order to be able to control the pump 41, 41*a*, the pump 41,41*a* may be provided with a control contact 42, 42*a* that can be connected to the control unit 12. In particular in case the control unit 12 controls the pump 41, 41*a*, the valve 39, 39*a* is optional in order to control the flow of material to be atomized towards the nozzle 38, 38*a*. Yet, the valve 39, 39*a* may be provided, for example in case the pump 41, 41*a* is manually driven by the user. For example, the pump 41, 41*a* may be a displacement or a micro-pump, for example a peristaltic pump. The pump could also be breath actuated, such that the underpressure caused by a puff drives the pump.

Upstream of the pump 41, 41*a*, a reservoir 43, 43*a* for the material to be atomized is arranged according to the exemplary embodiment. The reservoir 43, 43*a* may be a fillable or a refillable or an exchangeable or even a disposable tank, cartridge, container or capsule. In case the reservoir 43, 43*a* is exchangeable or disposable, information representing a desired particle size may be provided by the reservoir 43, 43*a*.

A gas or ambient air temperature sensor may be provided to determine the temperature of the gas ambient air outside of the aerosol generating component 2 or of the electronic smoking device 1. The ambient air temperature sensor, which is not shown in the figures for the sake of simplicity, may be connected to the control unit 12, preferably in a sensor signal transmitting manner. The control unit 12 may control at least one or even both of the atomizing elements 33, 33*a* and/or at least one or even both of the supply apparatuses 37, 37*a* in dependence of the ambient temperature in order to influence the particle sizes.

Alternatively or additionally, based on the sensor signal from the temperature sensor 35, 35*a*, the control unit 12 may determine the period necessary for reaching the predetermined operation temperature for at least one or even both of the atomizing elements 33, 33*a*. In case the period is either longer or shorter than expected, the control unit 12 can determine that the ambient temperature is either lower or higher than expected and can adapt the parameters of at least one or even both of the atomizing elements 33, 33*a* and/or at least one or even both of the supply apparatuses 37, 37*a* accordingly. For example, in case the period is shorter, the control unit 12 may determine that the ambient temperature is higher, and can adjust the operation parameters of at least one or even both of the atomizing elements 33, 33*a* and/or at least one or even both of the supply apparatuses 37, 37*a*, such that less energy is provided to at least one or even both of the atomizing elements 33, 33*a* and/or less material to be atomized is provided by at least one or even both of the supply apparatuses 37, 37*a*.

Figure 4:
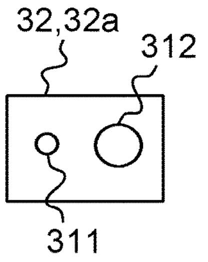
FIG. 4 is a schematic view of a first possible embodiment of a gas inlet element of the aerosol generating component.

FIG. 4 schematically shows a first exemplary embodiment of a gas inlet element 32, 32*a*. The gas inlet element 32, 32*a* of the exemplary embodiment of FIG. 4 is formed with two inlet openings 311, 312, which are differently dimensioned and in particular have different inner diameters. Such a gas inlet element 32, 32*a* may be moved with respect to the mixing chamber 30, 30*a*, such that a selected one of the inlet openings 311, 312 can be brought in communication with the inner volume of the respective mixing chamber 30, 30*a*. For example, inlet opening 311 may be brought in communication with the inner volume instead of inlet opening 312. Alternatively, one of the inlet openings 311, 312 may brought into communication with the inner volume in addition to the other one of the inlet openings 311, 312.

Figure 5:
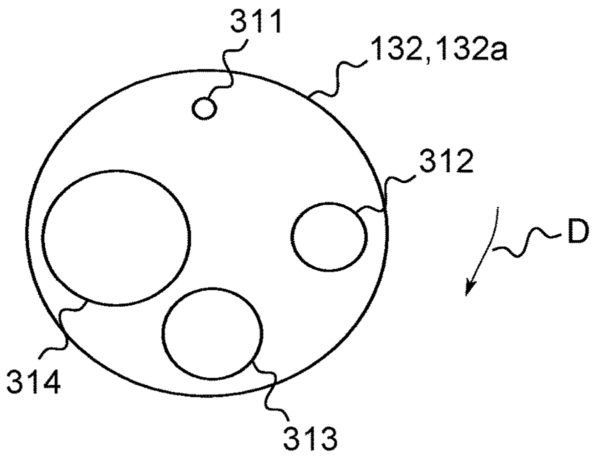
FIG. 5 is a schematic view of a second possible embodiment of a gas inlet element of the aerosol generating component.

FIG. 5 shows another exemplary embodiment of the gas inlet element 132, 132*a* in a schematic view. For the sake of brevity, only differences to the exemplary embodiment of FIG. 4 are discussed.

The gas inlet element 132, 132*a* of FIG. 5 has a circular cross-section and may be formed as a round disk or a cylinder. The gas inlet element 132, 132*a* may be rotatable or revolvable around an axis, for example a central axis of the gas inlet element 132, 132*a*, in order to bring selected inlet openings 311, 312, 313, 314 in communication with the inner volume of the respective mixing chamber 30, 30*a*. As shown in the exemplary embodiment of FIG. 5, the gas inlet element 132, 132*a* comprises more than one and for example four inlet openings 311, 312, 313, 314, which are differently dimensioned. For example, in a clock-wise direction D of the circular gas inlet element 32, inner diameters of the inlet openings 311, 312, 313, 314 may increase.

At least one and even both of the gas inlet elements 32, 32*a* shown in FIG. 3 may be replaced by at least one of the gas inlet elements 132, 132*a*.

Optionally, at least one of the first and the second atomizers 10, 11 may comprise a pre-heating element for pre-heating the gas, e.g. the ambient air, before it is led into the respective mixing chamber 30, 30*a* such that the gas led into the respective mixing chamber 30, 30*a* has a constant temperature that is independent of the temperature outside of the aerosol generating component 2 or of the electronic smoking device 1.

The dispensed material to be atomized may be atomized and for example vaporized in less than one second by the respective atomizing element 33, 33*a*. Preparing and for example heating the atomizing elements 33, 33*a* and blending the aerosols with each other and optionally with gas, e.g. ambient air, typically adds less than 2 seconds to the atomization of the material, such that the whole atomizing and provision of the aerosol to be inhaled takes no more than 2 seconds. Hence, the user can inhale the generated aerosol completely during one puff.

Preferably, the predetermined operation temperature of at least one of the atomizing elements 33, 33*a* and even of both atomizing elements 33, 33*a* is constant or equal, and the gas dilution of the atomized particles is different for the two atomizers 10, 11 in order to generate aerosols with different particle sizes due to the different inlet openings 31, 31*a*, 311, 312, 313, 314. In particular, the energy supply to the atomizing element is varied and the airflow is not varied.

Preferably, the quantity of the material, e.g. a liquid, to be dispensed and/or the predetermined operation temperature can be chosen by the user.

For example, in case a first of the materials to be inhaled is a flavor product, the particle size of the flavor product in the aerosol can be chosen to be large. For example, the size of the large particles may be larger that a size of smaller particles of the other aerosol. The size difference of small and larger particles such that the size of large particles corresponds to a percentage of the size of the smaller particles, wherein the size difference may be selected from a rage that can be formed by selecting any percentage listed in the following as upper and lower values of that range, namely 110%, 120%, 125%, 130%, 150%, 175%, 200%, 250%, 500%, 750% and 1000%. This, the size of the larger particles may correspond to the size of the smaller particles multiplied by and of the above mentioned percentages or a value therebetween. For example, larger particle may be larger than 5 μm, such that the first material is more likely to be deposited higher in the respiratory track (such as in the buccal and nasal cavity where the taste and smell receptors are located) and can improve the user's taste experience more efficiently. The second material to be inhaled may be a nicotine product, for example a product that contains a certain amount of nicotine, wherein the size of the particles of the second product in the aerosols may be smaller than the particle size of the first product and for example between 1 and 3 μm, such that the nicotine containing particles are more likely to be deposited in the lower respiratory tract where the transfer to the bloodstream is most efficient. For example, in case the sizes of the smaller particles is 1 μm, a larger particle with a size of 5 μm has a size that corresponds to 600% of the size of the smaller particles. Hence, less nicotine needs to be inhaled by the user in order to achieve a desired effect, compared to a traditional electronic cigarette where the particle size is not optimized for nicotine transfer to the blood.

The particle size preferably is a typical particle size of the material to be inhaled in the aerosol. For example, the particle size may be the mean particle size of the particles of one of the products to be inhaled. Alternatively, the particle size distribution may have its maximum value at the typical particle size of the particles of one of the products to be inhaled.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

The invention claimed is:

1. An aerosol generating component for an electronic smoking device, wherein the aerosol generating component is configured to generate two aerosols, a particle size of a first of the aerosols differing from a particle size of a second of the aerosols, and wherein the aerosol generating component comprises a first atomizer that is configured to generate the first aerosol, and a second atomizer that is configured to generate the second aerosol, wherein the first atomizer and the second atomizer each comprise a mixing chamber for mixing atomized material with gas and an inlet opening for supplying gas into the respective mixing chamber, the inlet opening of the first atomizer being configured to allow for generation of the first aerosol, and the inlet opening of the second atomizer being configured to allow for generation of the second aerosol; and wherein the size of the inlet opening of at least one of the first atomizer and the second atomizer is changeable.

2. The aerosol generating component according to claim 1, wherein at least one of the first atomizer and the second atomizer comprises a gas inlet element with at least two inlet openings, the gas inlet element being moveable with respect to the respective mixing chamber.

3. The aerosol generating component according to claim 1, wherein the first atomizer and the second atomizer each comprise an atomizing element for atomizing material for one of the aerosols, the atomizing element of the first atomizer being configured to allow for generation of the first aerosol, and the atomizing element of the second atomizer being configured to allow for generation of the second aerosol.

4. The aerosol generating component according to claim 1, wherein the atomizing elements are heating elements for atomizing material for the aerosols by evaporation.

5. The aerosol generating component according to claim 1, wherein the first atomizer and the second atomizer each comprise a supply apparatus for supplying material to be atomized, the supply apparatus of the first atomizer being configured to allow for generation of the first aerosol, and the supply apparatus of the second atomizer being configured to allow for generation of the second aerosol.

6. The aerosol generating component according to claim 1, wherein the aerosol generating component comprises a control unit for controlling process properties of at least one of the first and the second atomizers.

7. The aerosol generating component according to claim 1, wherein at least one of the atomizers comprises the heating element and a temperature sensor, the temperature sensor being connected to the control unit.

8. The aerosol generating component according to claim 1, wherein the aerosol generating component comprises a control unit for controlling process properties of at least one of the first and the second atomizers, and/or wherein at least one of the atomizers comprises the heating element and a temperature sensor, the temperature sensor being connected to the control unit and the control unit being connected to at least one of the supply apparatuses.

9. The aerosol generating component according to claim 1, wherein the control unit is configured to activate at least one of the supply apparatuses after at least one of the atomizing elements of the same atomizer has reached a predetermined operation state.

10. The aerosol generating component according to claim 1, wherein the aerosol generating component comprises a blending apparatus for blending the first with the second aerosol, the blending apparatus being configured to change the mixing ratio of the first and the second aerosols.

11. The aerosol generating component according to claim 1, wherein the first atomizer is different from the second atomizer in one or more of the parameters of:

A. operating temperature;

B. mixing chamber size and shape;

C. flow velocity through the mixing chamber;

D. liquid inflow supply rate;

E. temperature of intake air into the mixing chamber;

F. number, size and arrangement of intake openings into the mixing chamber.

12. An electronic smoking device comprising an aerosol generating component according to claim 1.

13. An aerosol generating component for an electronic smoking device, comprising:

a first atomizer adapted to generate a first aerosol having a first particle size; and a second atomizer adapted to generate a second aerosol having a second particle size different from the first particle size, via one or more of:

A] the first atomizer having a size and shape different from the second atomizer;

B] the first atomizer having an inlet opening size different from the second atomizer;

C] the first atomizer having a heater or ultrasonic vaporizer different from the second atomizer.

14. An aerosol generating component for an electronic smoking device, comprising:

a first atomizer adapted to generate a first aerosol having a first particle size; and a second atomizer adapted to generate a second aerosol having a second particle size different from the first particle size, via one or more of:

A] the first atomizer having a size and shape different from the second atomizer;

B] the first atomizer having an inlet opening size different from the second atomizer;

C] the first atomizer having a heater or ultrasonic vaporizer different from the second atomizer;

wherein a size of an inlet opening of at least one of the first atomizer and the second atomizer is selectable by the user and changeable manually.

* * * * *